United States Patent [19]

Laurance et al.

[11] Patent Number: 5,712,159
[45] Date of Patent: Jan. 27, 1998

[54] GLUCOSE RESPONSIVE INSULIN SECRETING β-CELL LINES AND METHOD FOR PRODUCING SAME

[75] Inventors: Megan E. Laurance, Portland, Oreg.; David Knaack, Chepachet, R.I.; Deborah M. Fiore, Swansea, Mass.; Orion D. Hegre, Chepachet, R.I.

[73] Assignee: Brown University Research Foundation, Providence, R.I.

[21] Appl. No.: 461,302

[22] Filed: Jun. 5, 1995

Related U.S. Application Data

[62] Division of Ser. No. 208,873, Mar. 10, 1994, Pat. No. 5,534,404, which is a continuation of Ser. No. 165,088, Dec. 10, 1993, abandoned.

[51] Int. Cl.$^6$ .............................. C12N 5/06; C12N 5/08; C12Q 1/54; C12P 21/00
[52] U.S. Cl. .............. 435/372.2; 435/3; 435/7.21; 435/14; 435/30; 435/34; 435/35; 435/69.4; 435/70.3; 435/325; 435/366; 436/172
[58] Field of Search .................. 435/3, 7.21, 14, 435/30, 34, 35, 69.4, 70.3, 240.1, 240.2, 240.21, 325, 366, 372.2; 436/172

[56] References Cited

U.S. PATENT DOCUMENTS

| | | | |
|---|---|---|---|
| 4,332,893 | 6/1982 | Rosenberg | 435/240.1 |
| 4,477,567 | 10/1984 | Healy | 435/70.3 |
| 5,229,365 | 7/1993 | Potter et al. | 514/12 |
| 5,534,404 | 7/1996 | Laurance et al. | 435/3 |

FOREIGN PATENT DOCUMENTS

| | | |
|---|---|---|
| 0 363125 | 4/1990 | European Pat. Off. |
| WO 9300441 | 1/1993 | WIPO. |

OTHER PUBLICATIONS

Alpert, S., et al., "Hybrid Insulin Genes Reveal a Developmental Lineage for Pancreatic Endocrine Cells and Imply a Relationship with Neurons", *Cell*, 53:295–308 (1988).
Asfari, M., et al., "Establishment of 2-Mercaptoethanol-Dependent Differentiated Insulin-Secreting Cell Lines", *Endocrinology*, 130(1):167–178 (1992).
D'Ambra, R., et al., "Regulation of Insulin Secretion from β-Cell Lines Derived from Transgenic Mice Insulinomas Resembles that of Normal β-Cells", *Endocrinology*, 126(6):2815–2822 (1990).
Efrat, S., "Beta–cell lines derived from transgenic mice expressing a hybrid insulin gene–oncogene", *Proc. Natl. Acad. Sci. USA*, 85(23):9037–9041 (1988).
Efrat, Shimon, et al., "Glucose Induces Insulin Gene Transcription in a Murine Pancreatic β–Cell Line", *The Journal of Biological Chemistry*, 266(17):11141–11143 (1991).
Gazdar, A., et al., "Continuous, clonal, insulin–and somatostatin–secreting cell lines established from a transplantable rat islet cell tumor", *Proc. Natl. Acad. Sci. USA*, 77(6): 3519–3523 (1980).

Hamaguchi, K., et al., "NIT-1, a Pancreatic β–Cell Line Established From a Transgenic NOD/Lt Mouse", *Diabetes*, 40:842–849 (1991).
O'Hare, M. M. T., et al., "Influence of a transplantable insulinoma on the pancreatic status of insulin and pancreatic polypeptide in the rat", *Diabetologia*, 28:157–160 (1985).
Hanahan, D., "Heritable formation of pancreatic β–cell tumours in transgenic mice expressing recombinant insulin/simian virus 40 oncogenes", *Nature*, 315:115–122 (1985).
Heimberg, H., et al., "Heterogeneity in glucose sensitivity among pancreatic β–cells is correlated to differences in glucose phosphorylation rather than glucose transport", Department of Biochemistry and Metabolism and Endocrinology, Diabetes Research Center, Vrije Universiteit Brussel and Laboratory of Physiological Chemistry, Université Catholique de Louvain and International Institute of Cellular and Molecular Pathology, B–1200 Brussels, Belgium, pp. 2873–2878.
Hicks, B. A., et al., "Transplantation of β cells from transgenic mice into nude athymic diabetic rats restores glucose regulation", *Diabetes Res. and Clinical Practice*, 14 pp. 157–164 (1991).
Hoffman, D., et al., "Transplantation of a Polymer–Encapsulated Cell Line Genetically Engineered to Release NGF", *Section of Artifical Organs, Biomaterials, and Cellular Technology*, Brown University, Providence, Rhode Island 02912; Neurology, Massachusetts General Hospital; and Surgical Division, University of Lausanne, Switzerland, pp. 100–106 (1993).
Ishihara, H., et al., "Pancreatic beta cell line MIN6 exhibits characteristics of glucose metabolism and glucose–stimulated insulin secretion similar to those of normal islets", *Diabetologia*, 36:1139–1145 (1993).
de Krijger, R. R., et al., "Enrichment of Beta cells from the human fetal pancreas by fluorescence activated cell sorting with a new monoclonal antibody", *Diabetologia*, 35:436–443 (1992).
Lacy, P. E., "Status of islet cell transplantation", *Diabetes Reviews*, 1(1):76–92 (1993).

(List continued on next page.)

*Primary Examiner*—Herbert J. Lilling
*Attorney, Agent, or Firm*—Ivor R. Elrifi; Leon R. Yankwich

[57] ABSTRACT

A cell culture of correctly regulated β-cells having enhanced secretion of insulin is described. A method of selecting such correctly regulated β-cells is also described comprising the following steps:

(a) providing a population of cells comprising β-cells in which increased intracellular concentrations of calcium ions is correlated with the extracellular presence of glucose;
(b) exposing the population to a vital calcium-activated labelling agent;
(c) exposing the population to glucose in a concentration sufficient to result in secretion of the insulin; and
(d) selecting from the population, cells which exhibit a higher level of intracellular free calcium or insulin secretion when exposed to said concentration.

5 Claims, 9 Drawing Sheets

OTHER PUBLICATIONS

Miyazaki, J-I., et al., "Establishment of a Pancreatic β Cell Line That Retains Glucose–Inducible Insulin Secretion: Special Reference to Expression of Glucose Transporter Isoforms", *Endocrinology*, 127(1):126–132 (1990).

Nielsen, D. A., et al., "Control of Insulin Gene Expression in Pancreatic β–Cells and in an Insulin–producing Cell Line, RIN–5F Cells", *The Journal of Biological Chemistry*, 260(25):13585–13569 (1985).

Omann, G. M., et al., "Pertussis Toxin Effects on Chemoattractant–Induced Response Heterogeneity in Human PMNs Utilizing Fluo–3 and Flow Cytometry", *Cytometry*, 12:252–259 (1991).

Pipeleers, D. G., "Perspectives in Diabetes 'Heterogeneity in Pancreatic β–Cell Population'", *Diabetes*, 41:777–780 (1992).

Power, R. F., et al., "Transgenic mouse model: a new approach for the investigation of endocrine pancreatic β–cell growth", *Gut*, 28(S1):121–129 (1987).

Radvanyi, F., et al., "Pancreatic β Cells Cultured from Individual Preneoplastic Foci in a Multistage Tumorigenesis Pathway: a Potentially General Technique for Isolating Physiologically Representative Cell Lines", *Molecular and Cellular Biology*, 13(7):4223–4232 (1993).

Sakurada, M., et al., "Relation between Glucose–Stimulated Insulin Secretion and Intracellular Calcium Accumulation Studied with a Superfusion System of a Glucose–Responsive Pancreatic β–Cell Line MIN6", *Endocrinology*, 132(6):2659–2665 (1993).

Wang, J. L., et al., "Glucose–induced Insulin Secretion from Purified β–Cells", *The Journal of Biological Chemistry*, 268(11):7785–7791 (1993).

Wang, J., et al., "Glucose–and Acetylcholine–Induced Increase in Intracellular Free $Ca^{2+}$ in Subpopulations of Individual Rat Pancreatic β–Cells", *Endocrinology*, 131(1):146–152 (1992).

Wollheim, C. B., et al., "Establishment and Culture of Insulin–Secreting β Cell Lines", *Methods in Enzymology*, 192:223–235 (1990).

Kiekens, R., et al., "Differences in Glucose Recognition by Individual Rat Pancreatic B Cells Are Associated with Intercellular Differences in Glucose–Induced Biosynthetic Activity." *J. Clin. Invest.*, 89:117–125 (1992).

Hiriart, M. et al., "Functional Subpopulations of Individual Pancreatic B–Cells in Culture." *Endocrinology*, 128(6):3193–3198 (1991).

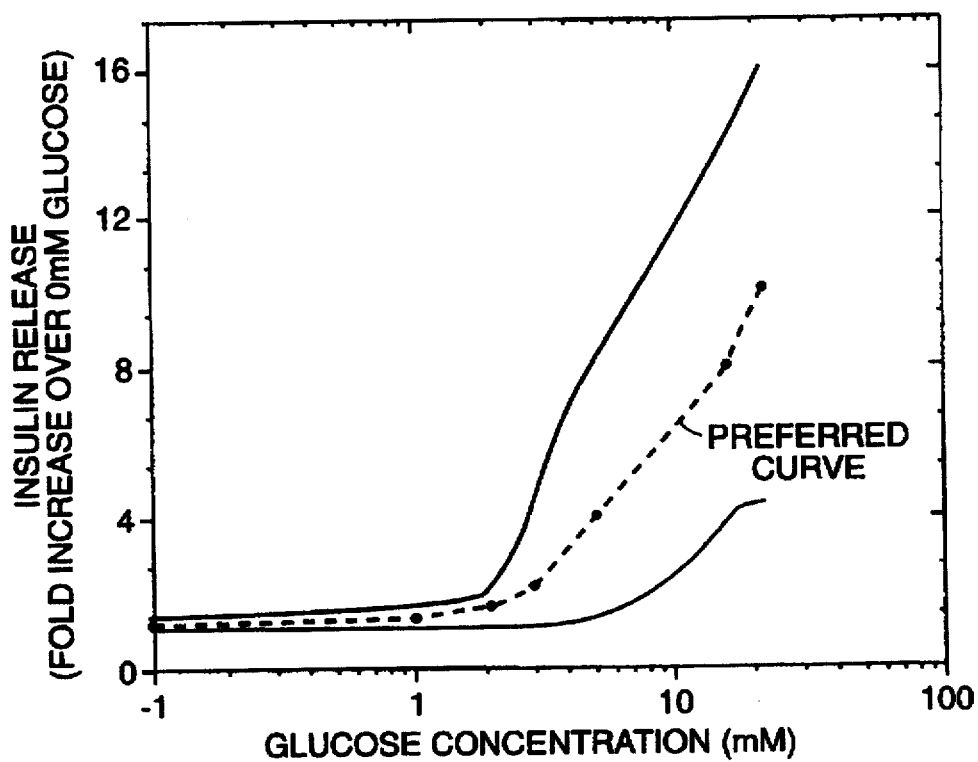
FIG._1
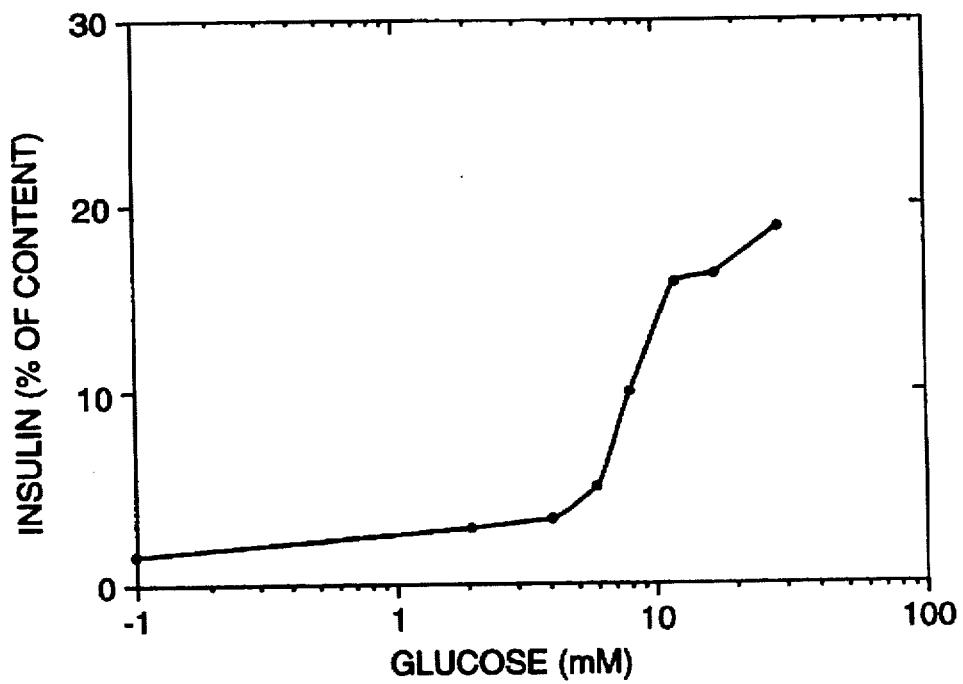
FIG._3

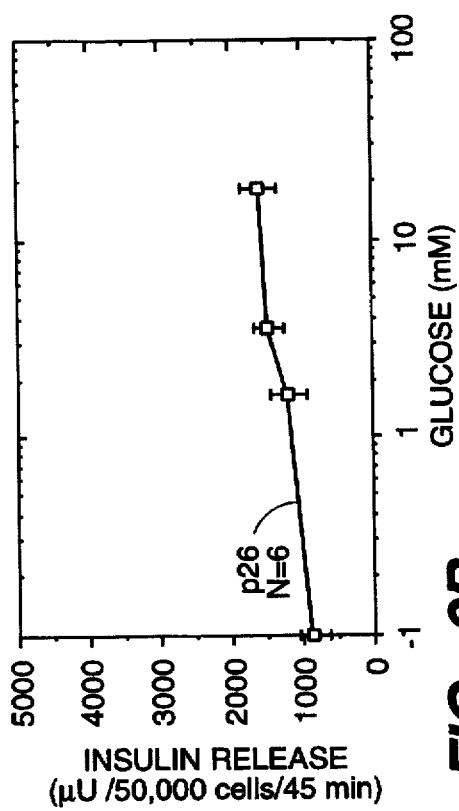
FIG._2B *(PRIOR ART)*
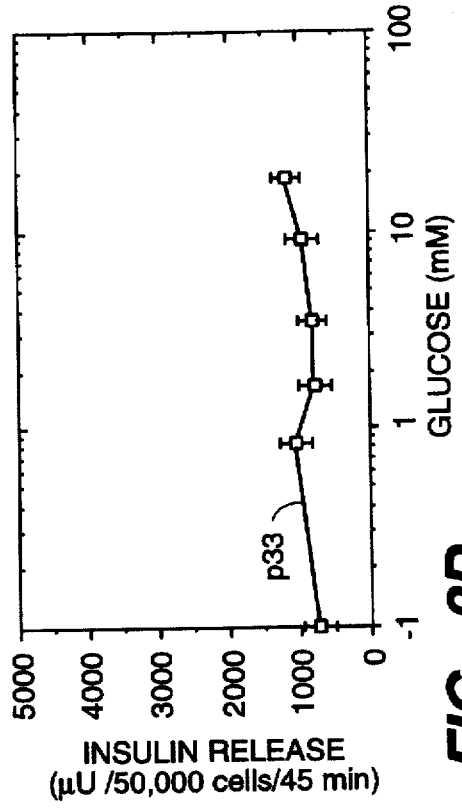
FIG._2D *(PRIOR ART)*
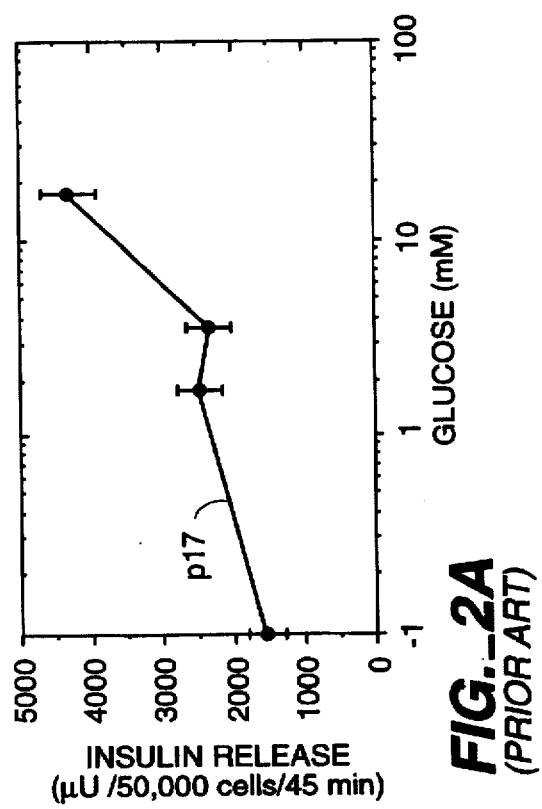
FIG._2A *(PRIOR ART)*
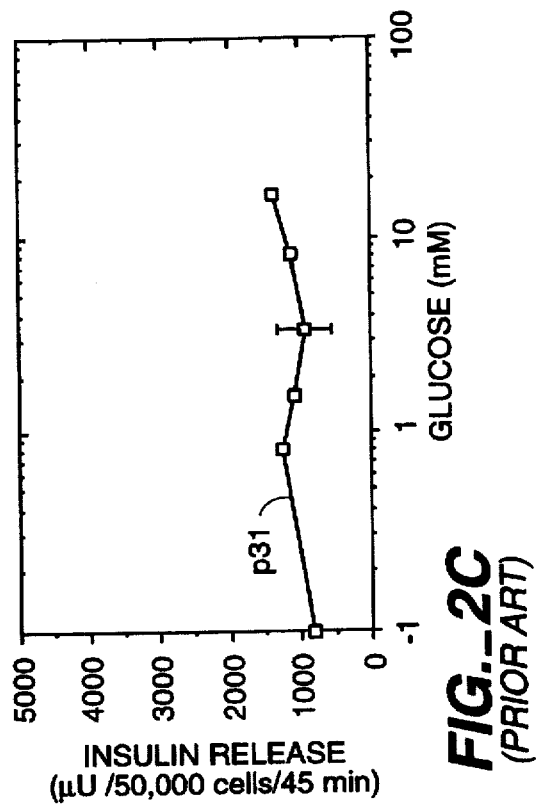
FIG._2C *(PRIOR ART)*

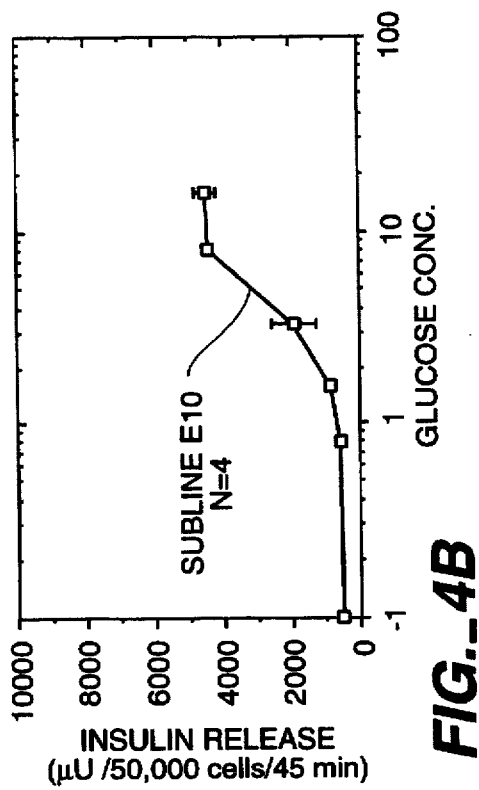
FIG._4A
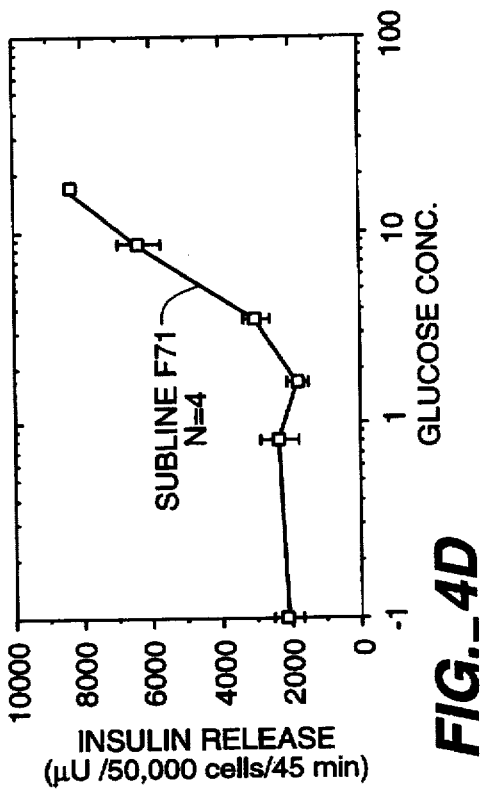
FIG._4B
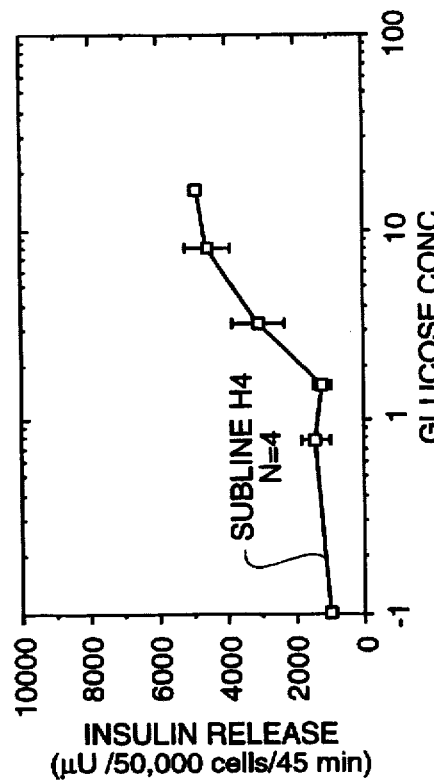
FIG._4C
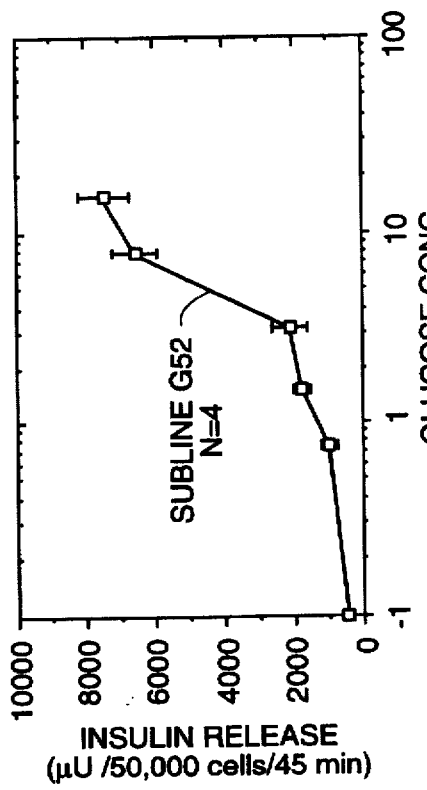
FIG._4D

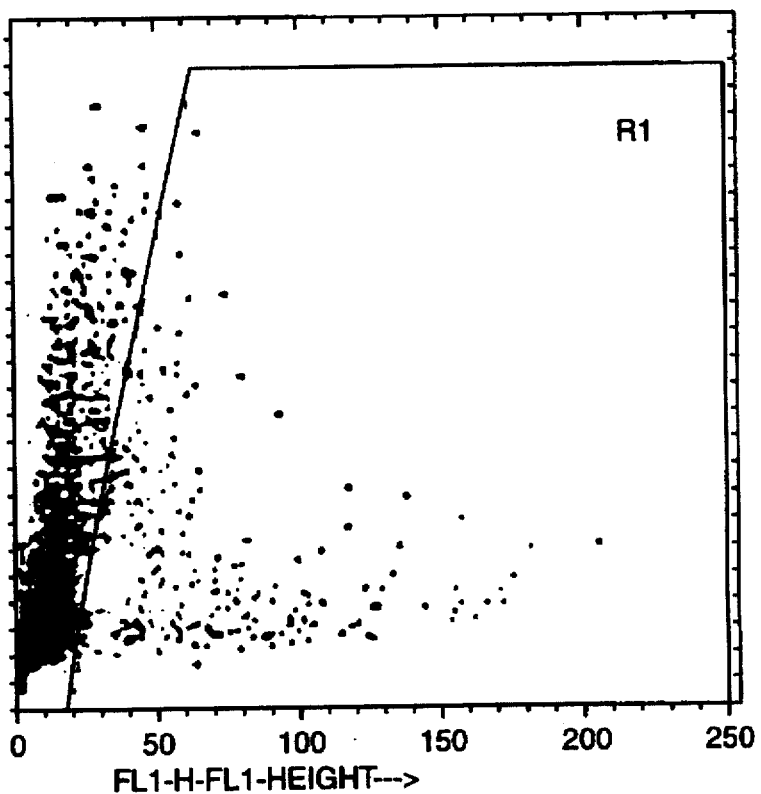
FIG._5A
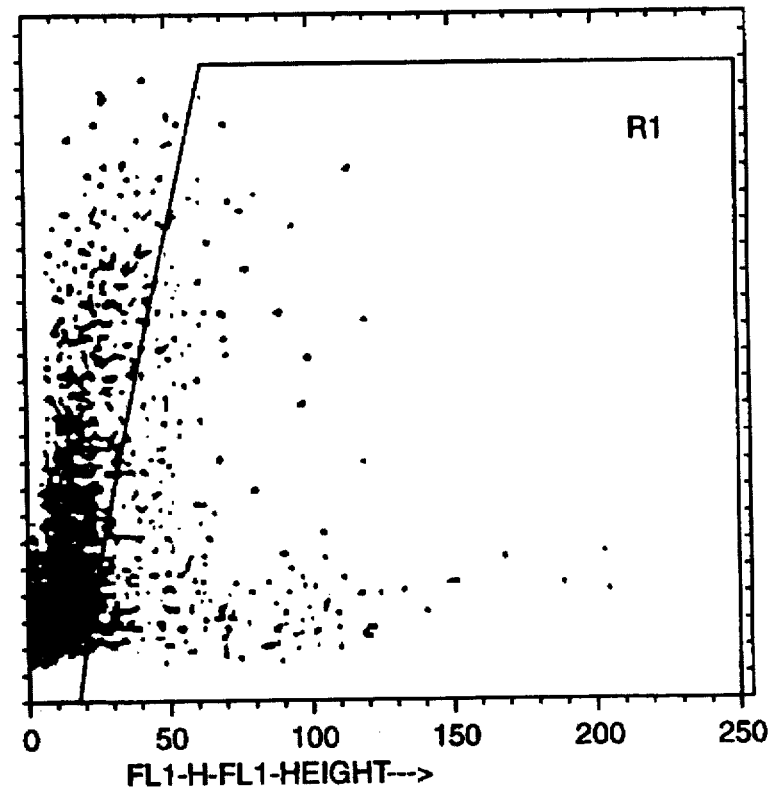
FIG._5B

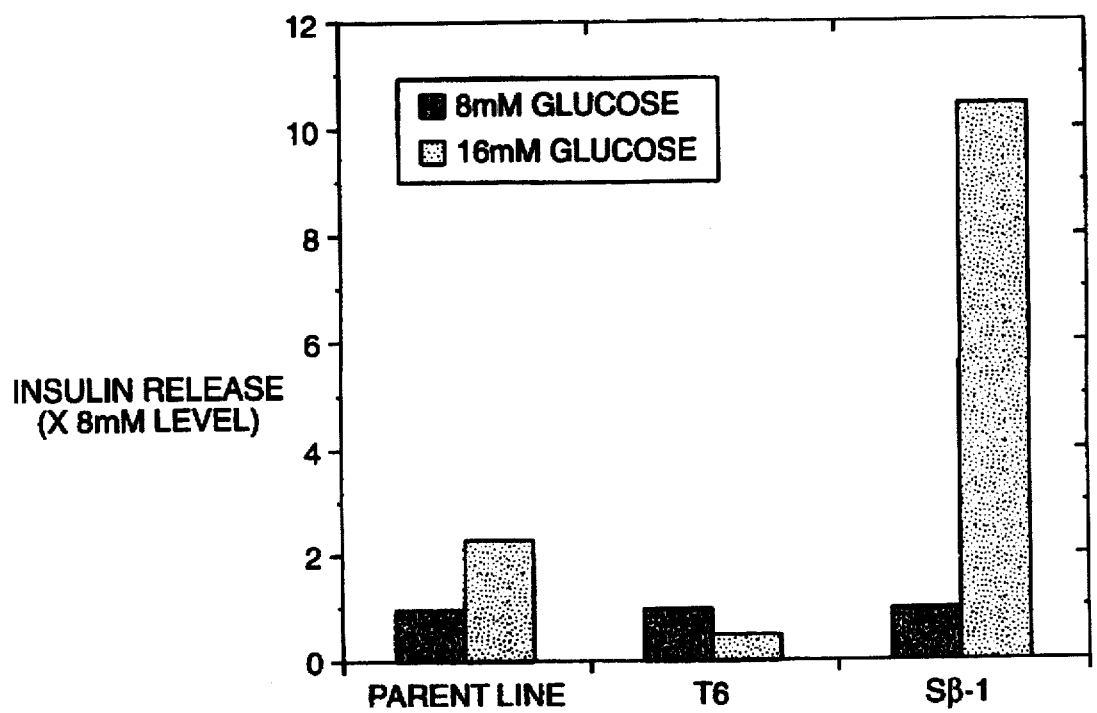
FIG._6
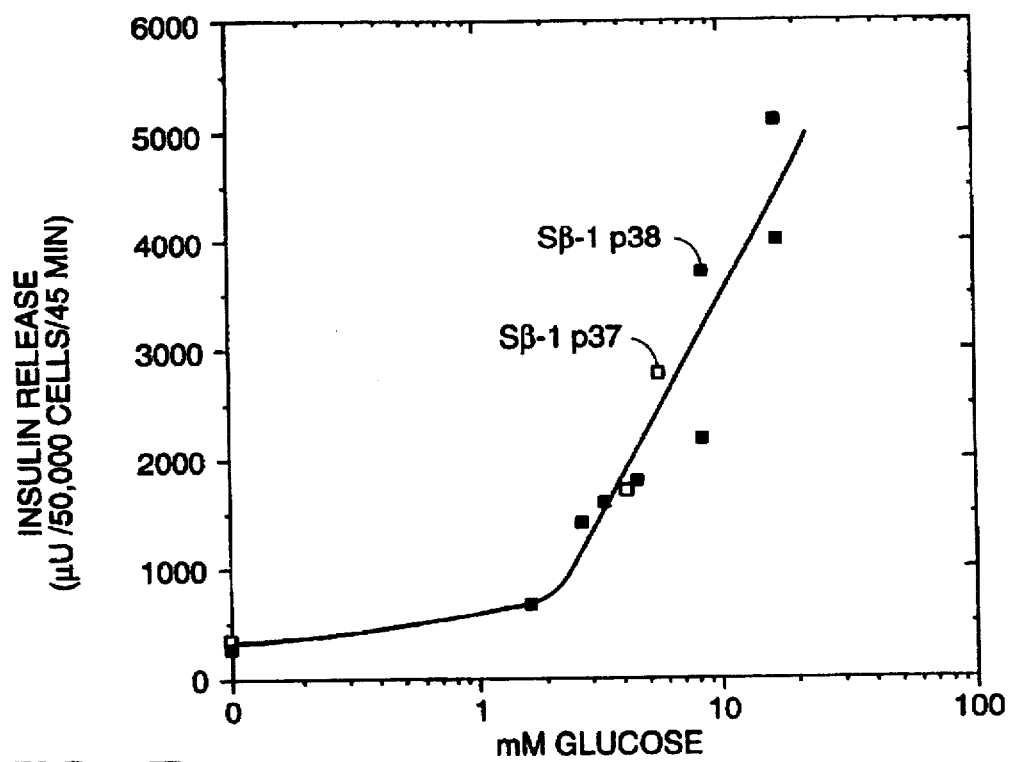
FIG._7

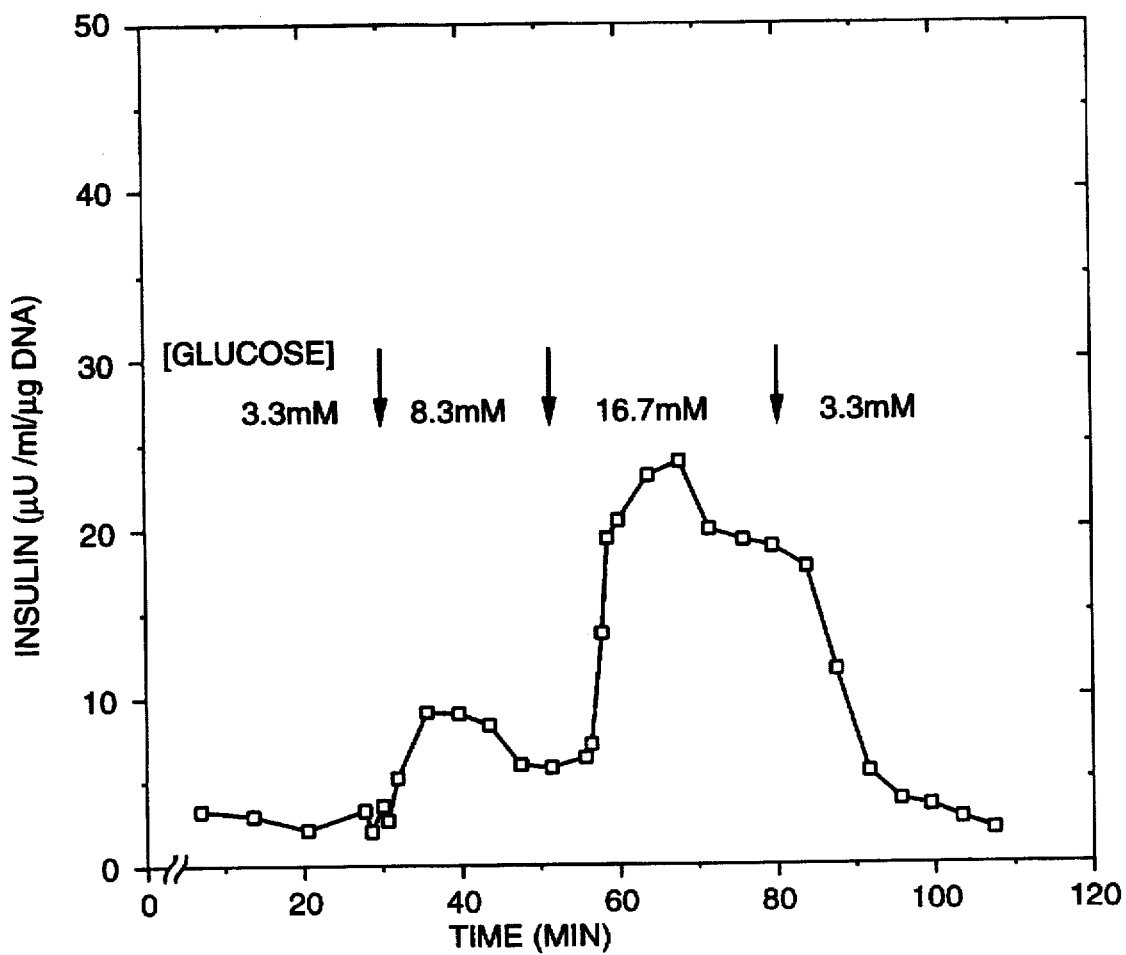
FIG._8

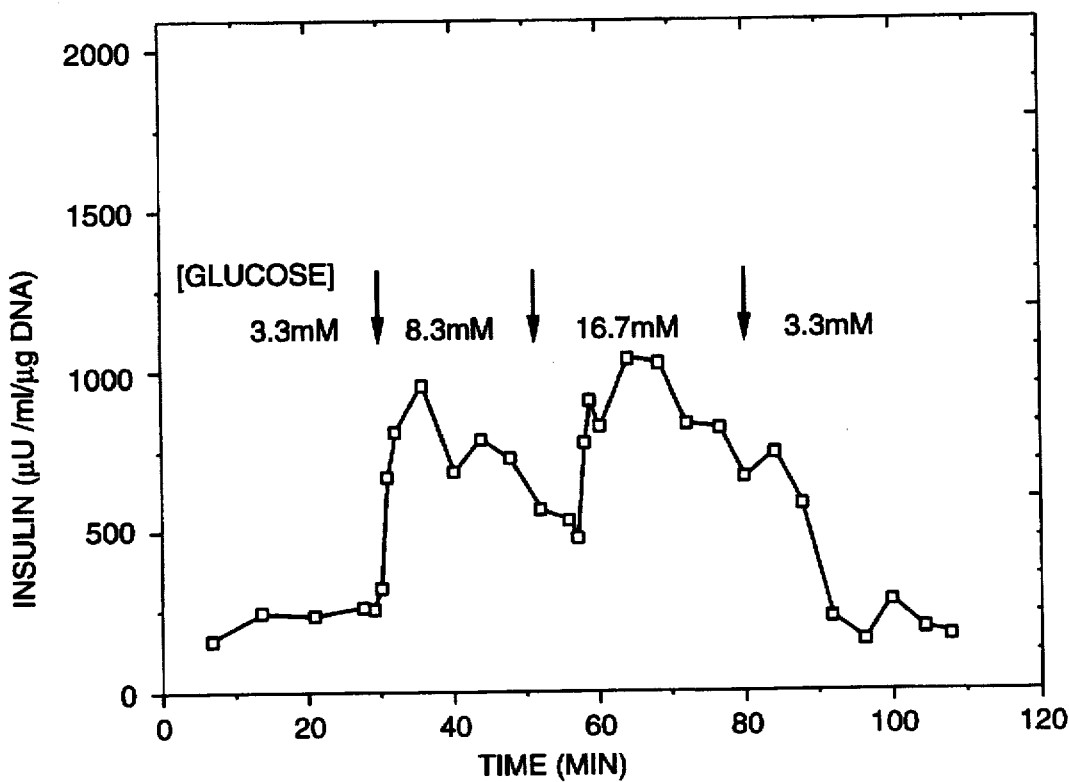
FIG._9
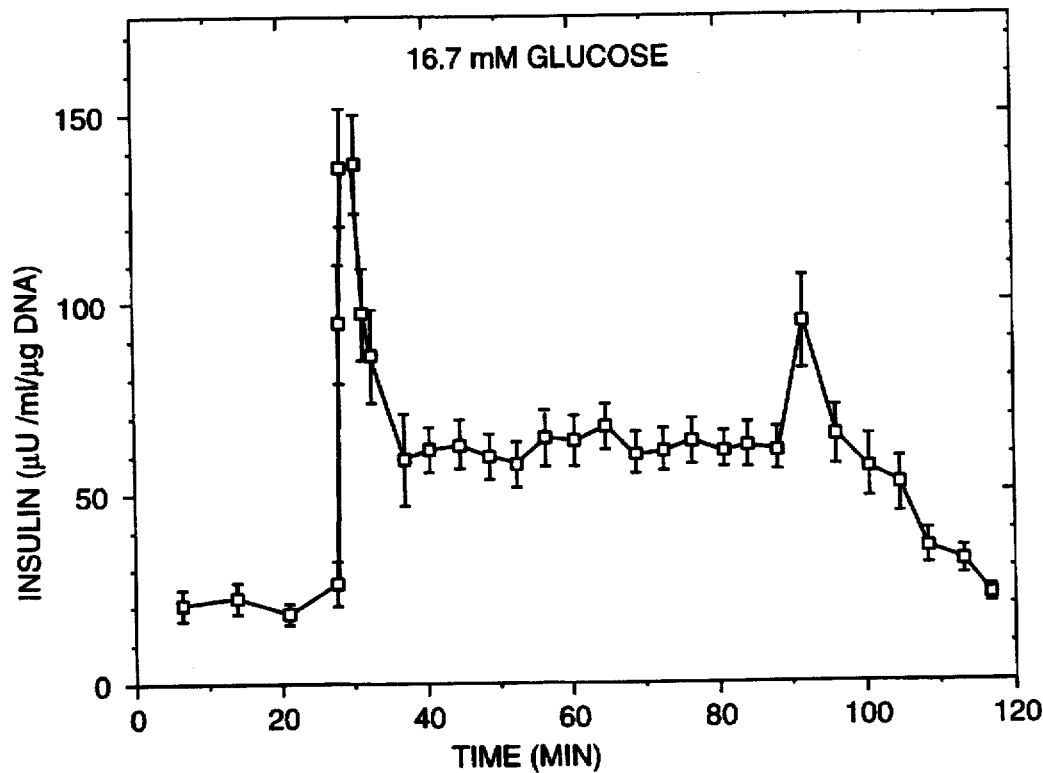
FIG._10

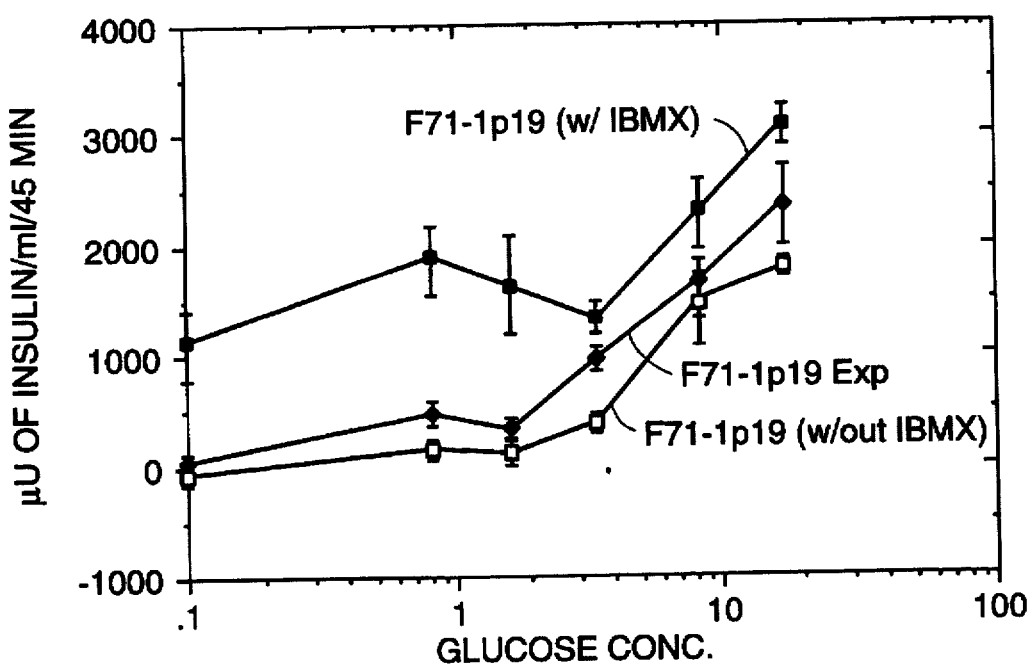
FIG._11
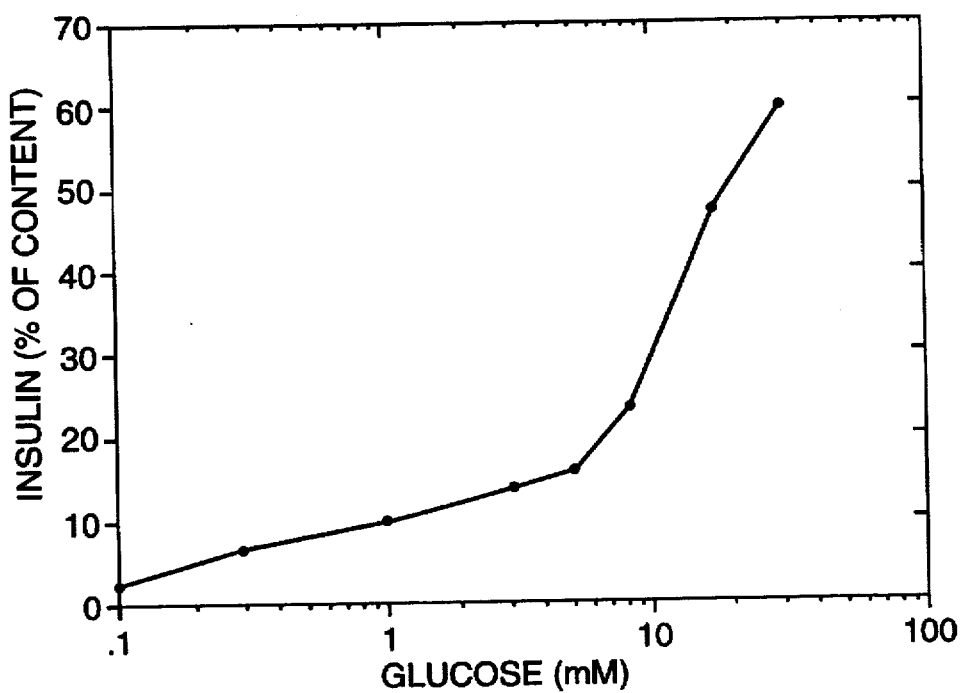
FIG._12

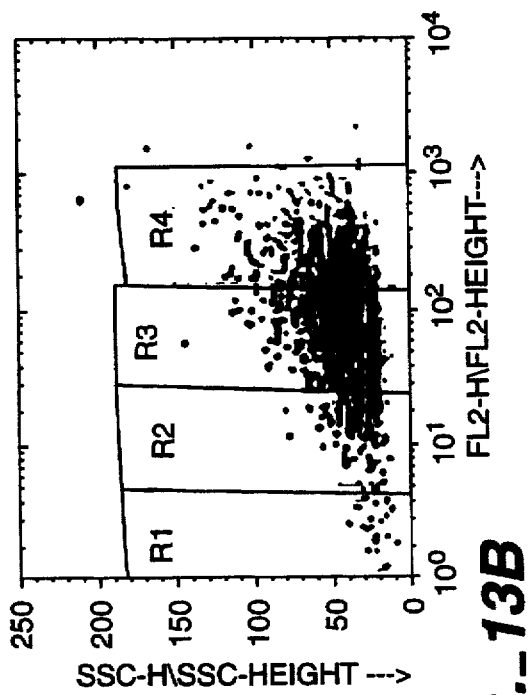
FIG._13B
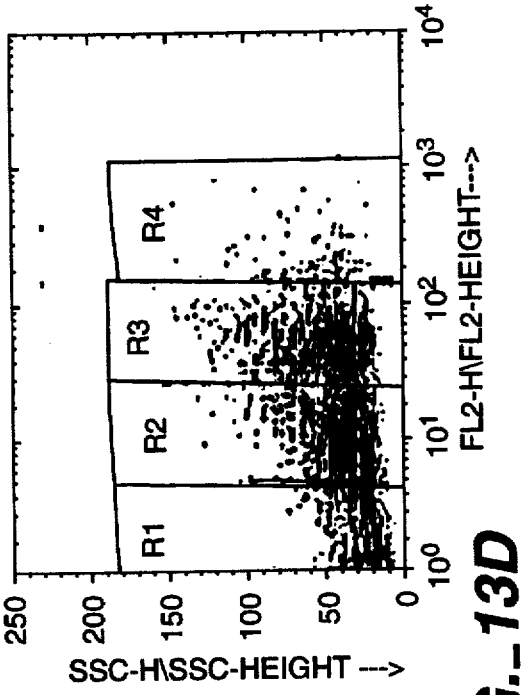
FIG._13D
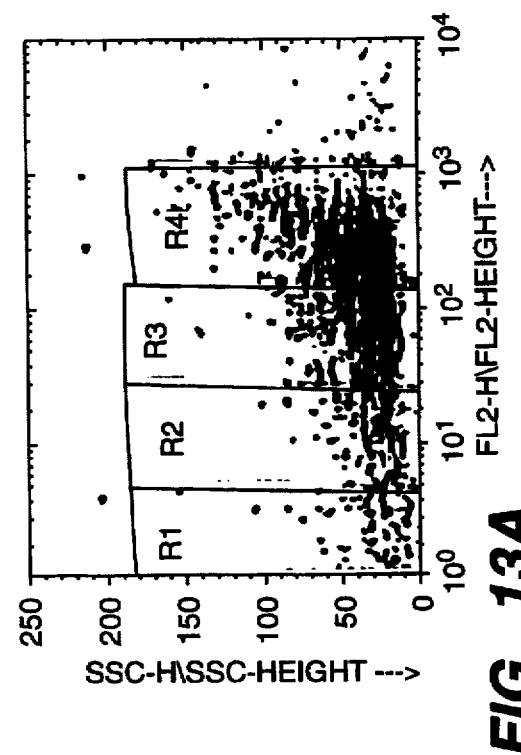
FIG._13A
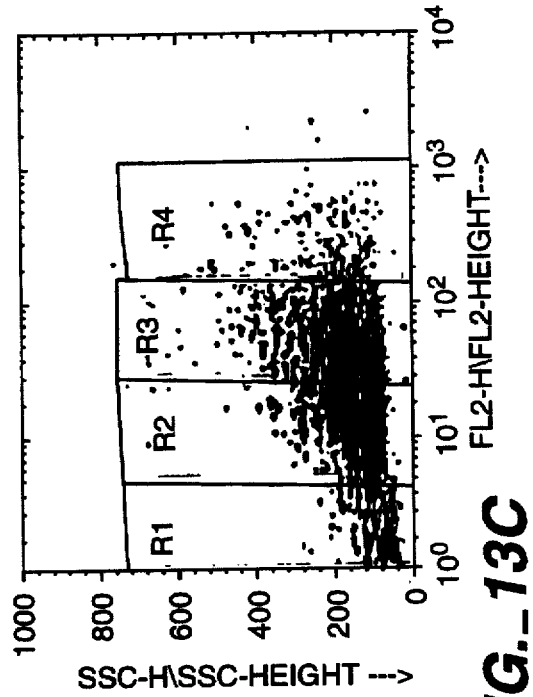
FIG._13C

GLUCOSE RESPONSIVE INSULIN SECRETING β-CELL LINES AND METHOD FOR PRODUCING SAME

This application is a division application of U.S. patent application Ser. No. 08/208,873, filed Mar. 10, 1994, now U.S. Pat. No. 5,534,404, which is a continuation application of U.S. patent application Ser. No. 08/165,088, filed Dec. 10, 1993, now abandoned.

BACKGROUND OF THE INVENTION

1. Field of the Invention

This invention relates to insulin-secreting β cells and methods of producing β cell populations having desirable features.

2. Description of Art

The insulin producing tissue of the pancreas, the islets of Langerhans, constitute a small fraction of the organ. Islets are largely composed of small clusters of β-cells and there is a need to develop a reliable source of β-cells which respond to glucose stimulation in a manner similar to that of normal islet cells for diabetes research and for implantation into diabetic subjects.

Populations of β-cells are known to show considerable heterogeneity in their morphology, their insulin secretion, and their glucose responsiveness. Normal islet tissue has been found to contain β cells which secrete insulin in response to glucose as well as some that do not. Individual glucose-responsive cells in the population have been shown to secrete insulin at different glucose levels. Pipeleers, "Perspective in Diabetes Heterogeneity in Pancreatic β-Cell Population", *Diabetes* (1992) 41:777–780. Islet cells in primary tissue culture show a characteristic sigmoidal curve upon glucose stimulation. As indicated in Wollheim, et al., "Establishment and Culture of Insulin-Secreting β Cell Lines", *Methods in Enzymology* (1990) 192:223–235, in a native β cell from all but the ruminants, the half-maximum level of insulin secretion is at about 7–8 mM glucose and the maximum is at a glucose level of about 15 mM or so (meaning that insulin secretion is about twice as much at 15 mM glucose as at 7–8 glucose). It is desirable, thus, that cells designed to mimic the activity of normal cells, either for implantation or for testing show a similar pattern of insulin secretion.

Historically, β-cells have been obtained by isolating them from primary tissue, employing collagenase digestion of the pancreas, a time-consuming and expensive process. However, while primary hormone-secreting cells can often be maintained for several months in culture, they generally undergo few or no cycles of cell division. During this time, the cells generally display a decrease in hormone secretion and/or a loss of regulation. For human transplantation purposes, researchers have investigated the use of both human and animal tissue. A major problem with the use of human tissue, however, is the shortage of available organs. Where animal tissue is used, extreme care must be taken to obtain material from pathogen-free animals and all isolated tissue must be extensively tested. Wang, et al., "Glucose- and Acetylcholine-Induced Increase in Intracellular Free $Ca^{2+}$ in Subpopulations of Individual Rat Pancreatic β-Cells", *Endocrinology* (1992) 131:146–152 and Wang, et al., "Glucose-induced Insulin Secretion from Purified β-Cells", *The Journal of Biological Chemistry* (1993) 268:7785–7791 and others have sorted β cells from other pancreatic tissue by fluorescence-activated cell sorting using inherent light-scattering patterns and flavin adenine dinucleotide autofluorescence. De Krijger, et al., "Enrichment of Beta cells from the human fetal pancreas by fluorescence activated cell sorting with a new monoclonal antibody", *Diabetologia* (1992) 35:436–443 has sorted human islet cells from other human pancreatic tissue by producing mouse monoclonol antibodies specific to the islet cells. The antibody was labeled and used for fluorescence-activated cell sorting, the resulting cultures showing an enriched β cell content. In general, though, these cells do not divide, and it is costly and time-consuming to repeatedly prepare β cells in this manner.

Some reports have indicated that β cells isolated from primary tissue can be made to divide in vitro. For example, Brothers, in "Hormone-Secreting Cells Maintained in Long-Term Culture", PCT Application WO 93/00441 published Jan. 7, 1993, selected and cultured cells from human pancreatic tissue without use of collagenase or centrifugation to establish subcultures of glucose-responsive cells cultured, at least originally, in media resembling the in vivo environment. Subsequently, individual cells or cell clumps in culture were selected for further propagation according to proliferation rate and amount of insulin secreted. Thawed cells which had been cryopreserved and cultured at passage 47 were tested for insulin secretion. Insulin secretion, according to the data presented, did not show the characteristic sigmoidal curve of correctly regulated cells, but rather what appears to be a horizontal line showing relatively static insulin secretion at different glucose levels. In addition, insulin levels are only at about $3.7 \times 10^3$ μIU/$1.5 \times 10^6$ cells/hour. Furthermore, these cultures were not free from contaminating non-β cells.

Zayas, et al., in "Proliferated Pancreatic Endocrine Cell Product and Process", EPO Application A2 0 363 125, published Apr. 11, 1990, discloses the culturing of pancreatic islet progenitor cells. These cells were proliferated in subculture in a collagen/laminate substrate gel to allow a three-dimensional culture system. The undifferentiated progenitor cells, when implanted, are reported to differentiate in vivo, resulting in in vivo insulin secretion.

Other researchers have attempted to overcome the problems associated with isolating natural islet cells by developing β-cell lines. A cell line offers several advantages over the use of primary tissue, as it provides a renewable source of cells having consistent properties. Attempts have been made to develop reliable cell lines from insulinomas. Wollheim, et al., supra, reports that a major problem with such cell lines, though, is the tendency of these cells to lose their differentiated status in culture, and a corresponding decrease in the cellular insulin content. As a result, most such previous approaches have achieved only limited success. After repeated passaging in vitro, these cell lines tend to show little or no insulin secretion, and/or a lack of desired insulin regulation in response to glucose.

Gazdar, et al., "Continuous, clonal, insulin- and somatostatin-secreting cell lines established from a transplantable rat islet cell tumor", *Proc. Natl. Acad. Sci. USA* (1980) 77:3519–3523 discloses the establishment of cell lines of rat pancreatic islet cells devoid of fibroblastoid cells by centrifuging to remove erythrocytes and enhancing growth by using feeder layers of rat liver cells. The final cultures were well-isolated colonies harvested and propagated to mass cultures. However, different sublines of the cell lines show different amounts of glucose responsiveness, and maximum insulin production shown after about 100 days was about 150 to 250 μU/$10^6$ cells/24 hours.

β-cell lines have been developed from X-ray induced mouse insulinomas as well as from insulinomas in transgenic mice expressing simian virus 40 T antigen. See Asfari, et al., "Establishment of 2-Mercaptoethanol-Dependent Differentiated Insulin-Secreting Cell Lines", *Endocrinology* (1992) 130:167–178, Hanahan, "Heritable formation of pancreatic β-cell tumours in transgenic mice expressing recombinant insulin/simian virus 40 oncogenes", *Nature* (1985) 315:115–122 and Efrat, et al., "Glucose Induces Insulin Gene Transcription in a Murine Pancreatic β-Cell Line", *The Journal of Biological Chemistry* (1991) 266:11141–11143. However, these cells (specifically RIN cells, HIT cells, β-TC cells, and INS cells) either do not show high insulin secretion or correct regulation and frequently do not retain their secretory characteristics over numerous passages. A discussion of the β-TC-3 cell line is found in detail in Efrat, et al., supra and numerous β-TC cell lines are discussed in D'Ambra, et al., "Regulation of Insulin Secretion from β-Cell Lines Derived from Transgenic Mice Insulinomas Resembles that of Normal β-Cells", *Endocrinology* (1990) 126:2815–2822. Although INS cells, particularly INS-1 show some degree of regulation, they do not show a large increase between half-maximum and maximum secretion and lower levels of secretion found in correctly regulated cells. In addition, the INS cells are mercaptoethanol-dependent for growth. Asfari, supra.

Some researchers have made specific attempts to overcome various of these problems. Miyazaki, et al., "Establishment of a Pancreatic β Cell Line That Retains Glucose-Inducible Insulin Secretion:Special Reference to Expression of Glucose Transporter Isoforms", *Endocrinology* (1990) 127:126–132 discloses two β-cell lines, called MIN6 and MIN7 obtained by targeted expression of the simian virus 40 T antigen gene in transgenic mice, the former obtained using "more than one cloning step", specific teachings of these steps being absent from the article. These cells have been characterized at 16–23 passages by Sakurada, et al., "Relation between Glucose-Stimulated Insulin Secretion and Intracellular Calcium Accumulation Studied with a Superifusion System of a Glucose-Responsive Pancreatic β-Cell Line MIN6", *Endocrinology* (1993) 122:2659–2665 and Ishihara, et al, "Pancreatic beta cell line MIN6 exhibits characteristics of glucose metabolism and glucose-stimulated insulin secretion similar to those of normal islets, *Diabetologia* (1993) 36:1139–1145. Additional information about these cells is found in Hamaguchi, et al., "NIT-1, a Pancreatic β-Cell Line Established From a Transgenic NOD/ Lt Mouse", The Jackson Laboratory, Bar Harbor, Me. (1991). According to Miyazaki, the MIN6 cells are regulated at 30 passages, although no data is presented to characterize the quality of regulation. It is interesting to note, as well, that while Ishihara has also characterized the MIN6 cells, and shown regulation at passages 16 to 23, the insulin output was significantly lower than initially reported by Miyazaki for these same cells at passage 16, suggesting some deterioration in insulin secretory response. However, at best these cells are reported to secrete about 1125 μIU of insulin/45 min/$10^5$ cells.

Increased intracellular free $Ca^{+2}$ ("cytosolic free calcium") is known to be induced by glucose in certain β cells. According to Wang, et al., "Glucose- and Acetylcholine-Induced increase in Intracellular Free $Ca^{2+}$ in Subpopulations of Individual Rat Pancreatic β-Cells", *Endocrinology* (1992) 131:146–152, p. 149, the pattern of response in β cells is similar to that of whole islets and isolated pancreas cells in prior studies. Wang, et al., "Glucose-induced Insulin Secretion from Purified β-Cells", *The Journal of Biological Chemistry* (1993) 268:7785–7791 has shown that β cells which do not show increased calcium concentration in direct response to glucose only may do so in the presence of other agents, resulting in increased insulin secretion in response to glucose stimulation. The presence of cytosolic free calcium in MIN6 cells (shown to be correctly regulated) and RINm5F cells (which have not shown high insulin secretion) was investigated by Sakurada, et al., supra. A close relationship between the rise of cytosolic free calcium concentration and insulin secretion was reported.

Omann, et al., "Pertussis Toxin Effects on Chemoattractant-Induced Response Heterogeneity in Human PMNs Utilizing Fluo-3 and Flow Cytometry", *Cytometry* (1991) 12:252–259 discloses the use of Fluo-3-acetoxymethyl ester (produced by Molecular Probes, Eugene, Oreg.), hereafter sometimes referred to as "Fluo-3", which binds with $Ca^{+2}$ in polymorphonuclear leukocytes for measurement of cytosolic calcium levels induced by N-formylpeptide.

Attempts have been made to transplant both insulinoma and normal islet cells into insulin-requiring organisms. The insulinoma transplanted into rats at an extrapancreatic site by O'Hare, et al., "Influence of a transplantable insulinoma on the pancreatic status of insulin and pancreatic polypeptide in the rat", *Diabetologia* (1985) 28:157–160 resulted in insulinaemia and hypoglycemia compared with controls. Undifferentiated pancreatic islet progenitor cells were transplanted into mice and allowed to differentiate in vivo for insulin production in vivo in Zayas, et al., supra.

The implantation of islet cells is discussed generally in Lacy, "Status of islet cell transplantation", 1 *Diabetes Reviews* (1993) No. 1, pp. 76–92. According to Lacy, to reduce rejection of foreign cells in the host organism, certain attempts have been made to reduce contact of the foreign cell with the host. For example, fetal rat islet cells encapsulated in microspheres have been transplanted into mice. Biocompatibility problems encountered were reduced by coating the microspheres with alginate. According to Lacy, mouse pancreatic cells encapsulated in hollow fibers had prolonged survival when transplanted into hamsters. Lacy indicates that suspending rat islets in alginate, however, while encapsulated in acrylic copolymer hollow fibers has been shown to maintain normoglycemia in diabetic mice, using even a subcutaneous site, normally a deleterious one for islet cells. In addition, Hoffman, et al., in *Experimental Neurology*, "Transplantation of a Polymer-Encapsulated Cell Line Genetically Engineered to Release NGF", (1993) 122:100–106, reports that the transplantation of rat fibroblasts or fibroblasts genetically modified to produce NGF (nerve growth factor) were loaded within a thermoplastic hollow fiber-based capsule.

However, in Hicks, et al., "Transplantation of β cells from transgenic mice into nude athymic diabetic rats restores glucose regulation", *Diabetes Research and Clinical Practice* (1991) 14:157–164, β-cells from the mouse pancreatic β-cell line βTC-1, one of the cell lines mentioned above (which does not show proper regulation and shows low insulin secretion according to D'Ambra, supra) attached to a collagen microcarrier and implanted in diabetic rats show improved insulin production and glucose response over diabetic rats implanted only with microcarriers, but showed increased granuloma formation and intense inflammatory reaction compared to diabetic controls without any implants.

It is thus apparent that there is still a need for the development of dividing β-cell populations resembling normal islet cell populations in insulin secretion levels and in correct insulin regulation in response to glucose, particularly such cells which are phenotypically stable over time and which can be repeatably and predictably produced, as well as implanted for the treatment of diabetes.

The references discussed above are provided solely for their disclosure prior to the filing date of the present application. Nothing herein is to be construed as an admission that the inventors are not entitled to antedate such disclosure by virtue of prior invention or that they are otherwise part of the prior art.

SUMMARY OF THE INVENTION

In one aspect, the present invention is a method of selecting cells with enhanced secretion of a secretory product including the following steps: (a) providing a population of cells including cells in which increased intracellular concentrations of calcium ions is correlated with the extracellular presence of a secretagogue; (b) exposing the population to the secretagogue in concentration sufficient to result in secretion of the protein; (c) selecting from the population, those cells which exhibit increased amounts of intracellular free calcium when exposed to the secretagogue in step (b); and (d) culturing the selected cells.

In another aspect, the present invention is a method of cloning β cells including the following steps: providing a population of β cells; proliferating the cells in the population on soft agar; selecting individual clusters of the cells in the population to create subclones; dissociating the subclones; and proliferating the subclonal cells to produce subclonal cell lines.

In still another aspect, the present invention is a method of producing a correctly regulated population of β cells including the following steps: (a) providing a population of correctly regulated β cells; and (b) selecting from the population, a group of cells which divide slowly relative to other cells in the population.

In still another aspect of the present invention, a method of providing a line of correctly regulated β cells including the following steps: providing a population of β cells; selecting from said population the cells which secrete approximately twice as much insulin when stimulated by glucose at a first concentration at a point above about 10 mM as they do when stimulated by glucose at a second concentration at a point in the range of about 3 mM to about 9 mM.

In yet another aspect of the present invention, a line of correctly regulated β cells is provided capable of secreting more than about 1300 μUnits of insulin/45 minutes/50,000 cells.

In yet another aspect of the present invention, a line of β cells is provided capable of maintaining insulin secretion levels of more than about 1300 μUnits insulin/45 minutes/ 50,000 cells for more than about 25 passages in culture.

In yet another aspect of the present invention, a line of correctly regulated β cells is provided capable of secreting more than about 20% of their insulin content in response to maximal levels of glucose.

In still a further aspect of the present invention, a collection of correctly regulated β cells is provided containing a vital dye.

Other aspects of the invention are provided to accomplish the desired goal set forth above.

BRIEF DESCRIPTION OF THE DRAWINGS

FIG. 1 is a graph illustrating the glucose responsiveness of a correctly regulated idealized islet cell. The dotted lines shows optimum glucose responsiveness, while the solid black curves illustrate the outer ranges of glucose responsiveness in cells considered to be "correctly regulated" in response to glucose.

FIGS. 2A through 2D are graphs illustrating the glucose responsiveness of prior art β-TC-6 cells at passages 17, 26, 31, and 33 respectively.

FIG. 3 is a graph of insulin released expressed as a percent of total cellular insulin content at various levels of glucose stimulation, of a clonal cell subline according to the present invention.

FIGS. 4A–4D are graphs of the glucose responsiveness of four selected clonal cell sublines according to the present invention.

FIGS. 5A and 5B are the dot plots of the flow cytometry data used in the cell sorting method of the present invention illustrating the increased number of cells having a fluorescent intensity labelled R1 at the maximal glucose level (FIG. 5B) versus the half-maximal glucose level (FIG. 5A).

FIG. 6 illustrates the relative insulin released at 16 mM glucose as compared to 8 mM, by the parent cells, the subline produced by sorting according to the present invention ("Sβ-1"), and another subline ("T6") produced by sorting more than about 10 minutes after the cells were exposed to glucose.

FIG. 7 is a graph illustrating the glucose responsiveness of cells produced according to the sorting method of the present invention at passages 37 and 38.

FIG. 8 is a graph of the insulin secretion of perifused cells produced by sorting according to the present invention, taken over time with stepped increases in glucose level.

FIG. 9 is a graph of the insulin production of perifused adult mouse islet cells in primary tissue culture over time taken at stepped increases in glucose level..

FIG. 10 is a graph of the average insulin production by perifused porcine islet cells in primary tissue culture in response to high but constant glucose stimulation over time for 22 separate islet isolations and perifusions.

FIG. 11 is a graph of insulin released versus glucose concentration in subclone F7-1 at passage 38 with and without exposure to IBMX and other secretagogues.

FIG. 12 is a graph of the amount of insulin released as a percent of total cellular insulin content in cells sorted according to the present invention at increasing levels of glucose, measured 12 passages after sorting.

FIGS. 13A–13D show dot plots of cells to be sorted according to rate of division using cell membrane markers according to the present invention.

DETAILED DESCRIPTION OF THE SPECIFIC EMBODIMENTS

Physiological characterization of β cells as they exist in the endocrine pancreas has led to a general understanding of the glucose response and insulin secretory dynamics required to maintain normal blood glucose levels. Studies on isolated islets in vitro have confirmed much of the understanding gleaned from in vivo studies, and additionally the transplantation of isolated human pancreatic islets which had previously been characterized in vitro allows the prediction of the insulin secretory dynamics that would be required for a dividing cell in order to be physiological or therapeutically useful. In general, then, useful β cells will release useful amounts of insulin in response to glucose with similar regulation characteristics as healthy non-dividing islet cells in vitro. Glucose regulation similar to islets in vitro will be referred to herein as "correct regulation." This characteristic response to glucose appears as a sigmoidal curve on a graph of insulin secretion versus glucose concentration.

The dotted line in FIG. 1 shows an idealized plot of insulin release at various glucose concentrations. In some embodiments, the instant invention provides for the preparation of cell lines which have glucose response characteristics which fall within the area bounded by the two solid lines. Such response characteristics are characterized herein as "correct regulation." In preferred embodiments, the cell lines have characteristics which are close to or the same as the dotted line. Thus, the cells of the instant invention exhibit maximal insulin release at about 10 mM glucose or more. "Half-maximal level"—(i.e., add quotation marks around the term). as used hereafter refers to (a) the glucose level at which the cells secrete about half the maximum amount when the level of maximum insulin release is at 16 mM glucose or less, or (b) the glucose level at which the cells secrete about one-half the amount of insulin they secrete in 16 mM glucose concentrations when the maximum secretion level is at more than 16 mM glucose.

A correctly regulated cell line according to the present invention shows a half-maximal amount of insulin secretion at a glucose concentration ranging from about 3 mM to 10 mM, preferably about 4 mM to 9 mM, and optimally about 5 to 6 mM. In a correctly regulated line, maximal insulin secretion occurs at a glucose concentration of about 10 mM or more, usually about 12 mM to about 20 mM, and optimally at about 16 mM. In addition, basal insulin release in correctly regulated cells is represented by the portion of the glucose response curve less than about 1 mM glucose. The transition of the slope of the line in the basal region (when glucose concentration<1 mM) to the slope at the half-maximal point is greater than 50% complete (change in slope>((half-maximal slope -basal slope))/2) at glucose concentrations greater than 1 mM, most preferably at concentrations greater than about 2 mM and most preferably at concentrations greater than about 3 mM. Finally, in a "correctly regulated" cell population, the maximum amount of insulin secretion is about 4 or more times, preferably 6 or more times, most preferably 8 or more times that at the basal concentration of glucose. By way of information, a 16 mM glucose concentration is equivalent to a 300 mg/dl glucose solution. This is a representative normal in vivo high blood glucose concentration, although diabetics will sometimes have a higher blood glucose concentration of about 400 mg/dl. Where a diabetic's blood level rises above 400 mg/dl level, there is substantial risk to the organism.

Prior cell lines (the RIN cell lines, the NIT cell lines, the HIT cell lines, the β-TC cell lines, the INS cell lines, the MIN cell lines) as discussed earlier have generally failed to simulate normal islet cells in one or more of the following respects: lower than desirable insulin secretion levels, instability of secretion characteristics in culture, incorrect regulation of insulin, lack of reproducible means for recreating the cell lines, and/or special culturing requirements. To date, researchers have not been able to obtain insulin production at levels above about 1125 μIU insulin/45 min/$10^5$ cells for numerous passages in culture in any cell line or population produced.

In one embodiment, the present invention is a repeatable method of producing a cell population or line which secretes a given protein, preferably insulin, at enhanced levels and/or in a correctly regulated manner, for enhanced numbers of passages in culture. The protein is produced in response to a "secretagogue" (hereby defined as a compound or composition in response to which the cells secrete the protein) which is preferably glucose, and the cells are preferably β cells.

In one preferred embodiment, the method of producing cells with enhanced secretion of a protein includes the following steps:

(a) providing a population of cells including cells in which increased intracellular concentrations of calcium ions is correlated with the extracellular presence of a secretagogue;

(b) exposing the cells to a secretagogue in concentration sufficient to result in secretion of the protein;

(c) selecting from the cells those which exhibit increased amounts of intracellular free calcium when exposed to the secretogogue in step (b);

(d) culturing the selected cells.

The population of cells provided in step (a) is a population of secretory cells in which increases in intracellular calcium are correlated with exposure to a secretagogue, i.e., in which increases in intracellular calcium are implicated in secretion of a desired protein, in response to application of a secretagogue. Examples of such cells are neurosecretory- or hormone-producing cells (which produce neurotransmitters or proteins). Examples of hormone producing cells are β cells and pituitary-derived cells. Secretory products for β cells include GABA (gamma-aminobutyric acid) as well as insulin. Adrenocorticotrophic hormone (ACTH) is secreted by the AT T20 cell line.

Examples of neurosecretory cells are adrenal chromaffin cells, neurons, glia, and the like. Adrenal chromaffin cells secrete opioid peptides such as enkephalin in response to nicotine or acetylcholine and also secrete epinephrine and norepinephrine while certain neurons secrete glutamate. Cells derived from adrenal medulla cells, as well as embryonic ventral mesencephalic tissues, and cells derived from the neuroblastic cells secrete dopamine. Examples of neurosecretory cell lines are GT-1 which produces gonadotropin releasing hormone (GNDH) and PC-12 which secretes dopamine. In the preferred embodiment, the cells are β cells and the secretory product is insulin. The secretagogue can be any of a number of compounds such as L-leucine, α-ketoisocaproic acid, d-glyceraldehyde, arginine, glucagon, gastric inhibitory peptide, carbamylcholine, and potassium (at high levels). The preferred secretagogue is glucose.

The starting population of β cells used preferably show measurable levels of insulin production, i.e., greater than 100 μIU/45 min/$10^5$ cells, preferably greater than 1000 μIU/45 min/$10^5$ cells, most preferably greater than 4000 μIU/45 min/$10^5$ cells, such as the β-TC-6 cell line. It is also preferable that the starting population of cells for the present invention show correct regulation at some passage. It Should be noted in this regard that the cells selected need not be selected at a passage in which they show correct regulation. In the preferred embodiment, the cells were sorted at passage 21, while regulation of the parent line deteriorated sometime between passage 17 and 26. (The word "passage" as used herein refers to the transfer of cells in culture from one media to another after reaching a growth-limiting concentration in the first media.)

FIGS. 2A through 2D illustrate insulin secretion of the β-TC-6 cell line used as a parent cell population in the preferred embodiment of the present invention. At passage 17 (see FIGS. 2A and 2B), it can be seen that the β-TC-6 cells show some insulin regulation and a sigmoidal curve in response to increased levels of glucose although the relative amounts of insulin secreted indicate that the cell population is not "correctly regulated" at passage 17. At passage 26 (see FIG. 2B), regulation has deteriorated, the sigmoidal curve disappearing, and at passages 31 and 33 (see FIGS. 2C and 2D) regulation has completely disappeared, low levels of insulin being secreted at all glucose levels. Thus, over numerous passages, control of insulin secretion in β-TC-6 cells has significantly degraded.

However, it is not essential that the present invention utilize an existing cell line or population as the parent population. Instead, a base population of cells can be produced for use as the parent population using known methods. For example, Efrat, S., Linde, S., Kofod, H., Specter, D., Delannoy, M., Grant, S., Hanahan, D., and Baekkeskov, S., "Beta-cell lines derived from transgenic mice expressing a hybrid insulin gene-oncogene", in *Proc. Natl. Acad. Sci. U.S.A.* (1988) 85:9037–9041, which is incorporated herein as though fully set forth, on page 9037 teach a method for producing β-TC cells which can be used as the parent population for the methods of the present invention. Likewise, Radvanyi, et al., (1993) *Molecular and Cellular Biology*, Vol 7., No. 7, pp. 4223–4232, which is hereby incorporated by reference as though fully set forth discloses a method for producing cell lines from hyperplastic β cell populations.

In the preferred method, the cells are exposed in step (b) to levels of the secretagogue which are known to stimulate protein secretion in the cells of interest.

Preferably, the above method includes a further step (e) of exposing the population to a calcium-activated labelling agent. The preferred labelling agents are vital (non-toxic) dyes which complex with $Ca^{+2}$ and fluoresce at certain wavelengths and thus can be utilized for fluorescence-activated cell sorting. An example is Fluo-3-acetoxymethyl ester ("Fluo-3") or other dyes such as Indo-1 acetoxymethyl ester ("Indo-1") all made by Molecular Probes, Eugene, Oregon. The dyes show sensitivity to calcium ions so that increases in calcium content at the levels of interest are visible. In one aspect, the present invention comprises correctly regulated cells, such as those of the present invention, including vital dyes.

In the preferred method of the present invention, the labelled cells are exposed to a lower and a higher secretagogue concentration. Preferably the lower concentration is at a half-maximal level and the higher concentration is at a maximal level. Cell labelling is then preferably assessed.

In the preferred embodiment, the sorting is accomplished by fluorescence-activated cell sorting. The preferred method is fluorescence-activated cell sorting using the calcium-activated labelling agents mentioned above. After flow cytometry at the half-maximal and maximal glucose levels, a fluorescent intensity is defined to determine which group of cells will be selected in the sorting method of the present invention. The fluorescent intensity is selected such that the number of labelled cells having more fluorescence than the selected amount in the higher secretagogue concentration is greater than the number having more fluorescence than the selected amount in the lower secretagogue concentration. Most preferably, the fluorescent intensity is selected to define a group of cells in the higher glucose concentration containing about 50% more cells than that found at the lower concentration. More preferably the selected group in the higher concentration contains about twice as many cells as in the lower concentration. Most preferably, the number of cells will be about 20 times greater in the higher compared to the lower concentration population.

Referring to FIG. 6A, a dot plot is shown of the flow cytometry of an embodiment of the present invention at a half- maximal glucose concentration, while FIG. 6B shows the dot plot at the maximal glucose concentration. The group of cells falling within the area labelled R1 is selected. 900 cells appear in R1 at the maximal glucose concentration while only 552 appear at the half-maximal glucose concentration.

The same technique can be used to select insulin-secreting cells correctly regulated for other secretagogues such as cholinergic agonists, amino acids, and peptides such as glucagon.

Another aspect of the invention is the cell populations or cell lines produced according to the above-described method. Insulin production in cells of the present invention is preferably more than about 900 μIU ("International Units")/45 min/50,000 cells plated, more preferably more than about 1300 μIU/45 min/50,000 plated cells, most preferably about 2000 μIU/45 min/50,000 plated cells. (It should be noted that cells produced by the above method were plated at 50,000 cells; and tested after dilution and proliferation. A sample is thus expected to contain about $10^5$ cells, due to the amount of proliferation so that actual preferred insulin level is about 2,000 μIU/45 min/$10^5$ cells, for example.) In another embodiment, the amount of insulin released from the cells is preferably about 20%, more preferably about 20%, or most preferably about 60 to 70% or more of the total insulin content as the maximum level of insulin secretion. The cells are also preferably correctly regulated.

The preferred cell populations or lines of the present invention have been found to maintain their insulin-producing characteristics and/or their correct regulation more than about 5, more preferably more than about 23, most preferably more than about 30 passages in culture after their preparation.

In another aspect, the invention is another method of producing a line of β cells which are high insulin producers and/or are correctly regulated over numerous passages in culture. The cell line is created by providing a population of β cells, growing the cell population or cell line in soft agar, dissociating the cells, preferably using trypsin, although other dissociating agents such as collagenase, pancreatin, or any enzyme generally useful for cell dissociation for tissue cultures can be used, cloning individual cell clusters, and selecting those with desired insulin-responsiveness. "Cloning" as used herein refers to the process of culturing individual cells taken from a group of cells, to form a line of identical cells. The subclonal cell lines produced have the characteristics described above and are another aspect of the present invention. In the preferred embodiment, approximately five of the 40 subclonal lines were selected to form the subclonal cell lines of the present invention.

The soft agar used has been found to allow the cells to grow in three-dimensional rather than flat clusters, and thus apparently to remain more differentiated during growth. Soft agar as used herein means agar which is sufficiently viscous to allow such three-dimensional growth and contains about 0.1 to about 1% of actual agar, most preferably about 0.3% agar. Soft agar is made by dissolving an appropriate amount of agar in water. Alternatives to soft agar may be alginate and agarose. In order to promote growth, a desirable agar will contain growth factors such as laminen, type 4 collagen and basic F6F or their equivalents. The preferred material is Matrigel™ produced by Collaborative Research which contains such growth factors.

During cloning, the cells are preferably fed with standard media such as Dulbecco's Modified Eagle's Medium ("DMEM") having about 5 to about 30%, preferably 10% by volume conditioned media from other β cells, such as β-TC-3 cells. The conditioned media is believed to help maintain the differentiation of the cells in culture. After growing in this media, the cells are harvested and tested for insulin secretion. Clones are then selected for insulin production, subclones having high insulin production being desirable; in the preferred embodiment, subclones showing about twice as much insulin production at the maximal glucose level as at the half-maximal level of glucose solutions are selected. Data showing results of such screening for the parent line, and cells of the present invention is graphed in FIG. 7.

In the preferred embodiment, a β cell line is produced with correctly regulated insulin production over numerous passages in culture or in vivo and the cell line or population itself is another aspect of the invention. The cell line produced shows the insulin secretion levels discussed above.

Another embodiment of the invention is a method of producing a population, preferably a cell line, of correctly regulated β cells having high insulin secretion, preferably a cell line of such cells. In this embodiment, correctly regulated cells are selected according to their rate of division. Generally, the method includes selecting a correctly regulated starting population such as that produced according to the sorting or cloning methods of the present invention. The method includes the step of selecting these cells, if they are slowly dividing; otherwise dividing them into a rapidly dividing and a slowly dividing population, and selecting slowly dividing subpopulation producing more insulin than the rapidly dividing subpopulation.

In the preferred embodiment, selecting is accomplished using fluorescence-activated cell sorting and a cell membrane marker. The cell membrane marker is placed in solution with the cells to label the cell membrane in a fashion which is visible in the cell sorter. Flow cytometry data on the labelled cells is obtained immediately after marking. A portion of the cells showing high marking (Gate R4 on FIG. 14A) is selected. The selected cells are then allowed to proliferate. In the preferred embodiment, any vital cell membrane markers can be used in a fashion known in the art but the preferred cell membrane marker is PKH26-GL produced by Molecular Probes, Eugene, Oregon. Cells are usually exposed to the marker in concentrations which render them visible under fluorescence.

Using the sorter, the cells (preferably those selected as R4), after proliferation, are divided into two populations according to the amount of labelling, the highly marked population being the one that is selected. In the preferred embodiment, the cells selected show a half-life decay of fluorescence intensity which is greater than about 30%, more preferably greater than about 100% of the mean doubling time of the population. FIG. 14 is a dot plot of the results of flow cytometry of cells produced according to the above invention. In FIG. 13A, gate R4 shows the high fluorescence of most of the cells of the present invention immediately after labelling while gates R1 through R3 illustrate lower levels of fluorescence. After a few days of culturing (FIG. 13B), fewer cells show the high fluorescence level of gate R4. After another week in culture (FIG. 13A), the bulk of the cells show fluorescence clustering around gate R2 and R3; only a few cells show the high fluorescence of gate R4. After 2 weeks in culture, only a few cells show the high fluorescence of gate R4 (FIG. 13D) and they are selected.

In another embodiment, the present invention is a method of producing high insulin producing and/or correctly regulated, stable cell lines from a parent population of β cells by selecting the cells in which about twice as much insulin is secreted in about a 10 mM or more glucose solution as in about 3 mM to about 9 mM. Preferably, the first glucose concentration is about 12 mM to about 20 mM and the second concentration as about 5 mM to 9 mM. Most preferably, the first glucose concentration is about 16 mM and the second concentration is about 5–6 mM, the first concentration usually being at the maximal level and the second being at the half-maximal level. The cells are preferably selected according to the above-mentioned sorting or cloning processes.

In another embodiment of the invention, cells produced according to the present invention are enclosed in biocompatible insulin-permeable membranes for implantation. The membranes are preferably hollow fiber membranes or flat sheets which are considered particularly appropriate for implantation into humans. Preferred materials, the construction of the devices and, and the manner of enclosing the cells within them are disclosed fully in U.S. patent application Ser. Nos. 08/082,407, filed Jun. 23, 1993 and PCT/US92/03327, filed Apr. 22, 1992, and incorporated herein as though fully set forth. Generally, the cells of the present invention will be loaded into the device in the presence of soluble alginate which can subsequently by polymerized by placement of the device into a calcium chloride containing medium.

In another embodiment, the invention is a method of treating diabetes by implanting the encapsulated or enclosed cells described above. Numbers of cells and encapsulating devices to be implanted are preferably determined by traditional methods for determining insulin dosage in a diabetic patient. Large scale devices can be prepared as described in U.S. Patent Application PCT/US92/03327 above, and implanted into peritoneal or subcutaneous locations. Sufficient cells will be placed within the device so that patients will achieve normolycemina over a twenty-four hour period. The exact size of the device to deliver the proper dose will be determined empirically, but comparison of the insulin output of small devices used to cure diabetes in rodents (see U.S. patent application Ser. No. PCT/US92/03327, supra) will allow appropriate scaling for the body weight of a patient.

Implanting is accomplished by surgical methods known in the art.

EXAMPLES

Example 1: Selection of Subclones of β-TC-6.

β-TC-6 cells were obtained and cultured. Glucose responsiveness was tested at passages 17, 26, 31, and 33 by a modification of the method of Efrat, et al. (1993) as shown in FIGS. 2A through 2D. Briefly, cells were plated in 24 well falcon tissue culture plates at a density of 50,000 cells/well. The media was removed and cultures were rinsed 2–3 times with either Krebs solution, or Modified Eagle's Medium (MEM) containing 10% horse serum and 25 mM Hepes. Then, 1.5 ml of MEM with 10% HS and 0.5 mM IBMX was added to each well and cells were returned to the incubator. After 30 minutes, 0.5 ml of media was removed from each well (preincubation samples), and the glucose concentration of the remaining media in the wells was adjusted using a 30 mg/ml glucose stock and cells were returned to the incubator for an additional 45 minutes. At that point, media was harvested and assayed for insulin content using a radio immunoassay. The insulin released during the 45 minute incubation period was then calculated by subtracting the preincubation values from the 45 minute sample. Generally, 4 wells were used per glucose concentration. While passage 17 showed some regulated insulin production, regulation was not "correct" as discussed above and passage 26 showed deteriorating insulin production. Passages 31 and 33 showed poor regulation, with little or no increased insulin production upon exposure to increased levels of glucose.

About 60,000 passage 18 cells were suspended in 9 mls pre-warmed "complete" media at 37° C. (Complete media was Dulbecco's Modified Eagle's Medium ("DMEM"), Gibco No. 320-1965 with 15% horse serum by volume (all references to solutions and percentages herein are by volume, unless indicated otherwise) 2.5% fetal bovine serum (Gibco) and 10% conditioned media from β-TC-3 cells.) A half mil of Matrigel™ (Collaborative Research) was added to the solution. Soft agar was made by dissolving an appropriate amount of agar (made by Batco) in water. The cell suspension previously made was then mixed with the agar solution. 1.5 mls of the agar/cell solution was then placed in each well of a well plate.

Cells were allowed to grow in the agar for three weeks, being fed with 10% conditioned media twice a week. Individual cell clusters were harvested by pipet, and each cell cluster was placed in a well of a well plate to create a subclone, 40 subclones being created. Clusters were broken apart and fed three times a week with the above media, allowed to proliferate, and then split to expand the number of cultures. Each subclone was tested as a single well in a serial glucose response assay. Wells containing the cells of interest were rinsed several times with glucose-free Krebs or MEM containing 10% horse serum and 20 mM HEPES. 1 ml of the same medium was then added to the cultures for 30 minutes. At that time, 0.5 mls of the media was removed (preincubation) and 0.5 mls of fresh medium containing 6.4 mM glucose was added to the well to give a final glucose concentration of 3.2 mM. Cells were then incubated for 30 minutes to 1 hour in the incubator at which time 0.5 mls was sampled and 0.5 ml of fresh media was added back containing enough glucose to give a final concentration of 8 mM glucose. The incubation period was repeated and a third sampling was performed at which time the glucose concentration was adjusted to 16 mM with another 0.5 ml of glucose containing medium. All samples were frozen and subsequently assayed for insulin content. Amounts of insulin released during a given incubation were calculated by subtracting the residual insulin levels from the newly released amounts.

Individual wells containing subclones showing about twice as much insulin secretion in 16 mM glucose solutions as 8 mM glucose solutions were selected in order to develop the cell lines of the present invention. Once the cloned line has been expanded to the point that appreciable levels of insulin can be detected (e.g., 5,000–50,000 cells or ~14–17 doublings) a single culture can be assayed using a serial glucose challenge where, following a rinse procedure, the same culture is exposed to stepwise increases in glucose concentration and a sample of the media is removed before each increment in glucose concentration, and insulin release values calculated. Useful concentrations for such assays include a low value such as 3.2 mM glucose or less, a value of glucose around the expected half-maximal response such as 8 mM and a maximum stimulatory concentration such as 16 or 20 mM. In such serial assays where a relatively small number of cells are being assayed, sometimes artificially elevated insulin levels are encountered in response to the first (i.e., lowest) glucose concentration. Therefore, generally it is best to consider only the insulin output at the anticipated half-max and maximal values. Those populations with greater than a two-fold difference between an 8 mM and 16 mM glucose concentration can be considered as likely to be correctly regulated and the cultures can be further expanded for determination of complete glucose response curves.

The selected subclones were then cultured in the complete media mentioned above. At passage 32 (13 passages after cloning), they were tested for glucose-responsiveness using the assay method mentioned above. The cells were still correctly regulated, and a sigmoidal insulin response curve was obtained. FIGS. 4A and 4B illustrate the insulin response curve for four of the subclones at passage 32 in the culture. Maximum insulin secretion ranged from about 4500 to about 8200 μIU insulin/45 min/50,000 cells plated. FIG. 3 illustrates the percent of intracellular insulin released by subclone F7-1, one of the selected subclones.

Example 2: Selection and Cloning of Cell Lines by Calcium Activated Fluorescent Cell Sorting Preparation of Cells to be Stained β-TC-6 cells at passage 21 were trypsinized and resuspended in cell culture media, taking care to make a single cell suspension. Cells were counted and approximately $1-2 \times 10^6$ cells were placed in each tube. One tube was retained as a background control and was unstained. Cells were washed twice with Hanks' Balanced Salt Solution (HBSS) with 1% serum.

Preparation of Dye Stock

Immediately prior to staining the cells, the stocks and working solutions were made. To a 50 microgram aliquot of Fluo-3 acetoxymethyl ester™ made by Molecular Probes (F-1242, stored desiccated in freezer) were added, in order:

35 microliters of Pluronic F-127™ stock (Basfyandott) (stored in scintillation vialwrapped in foil). Pluronic is a non-ionic, high molecular weight surfactant polyol useful for helping solubilize water-insoluble dyes.

113 microliters fetal bovine serum (FBS) The latter was pipetted up and down to reconstitute the dye. The dye was orange in color when fully resuspended. The stock was wrapped in foil and placed in the freezer.

Preparation of a Working Solution

To make a 1.2 micromolar working solution, 30 microliters of the dye stock was added to 10 mls of HBSS with 1% serum. The vessel was wrapped with foil and held at room temperature.

Staining of Cells 1 ml of the 1.2 microMolar working solution of Fluo-3 was added to each pellet of cells (except for the background cells). The tubes were shaken lightly to disperse the dye. The tubes were wrapped in foil, and allowed to sit at room temperature for 30–45 minutes. The cells were washed with HBSS with 1% serum at 1000 rpm for 5 minutes. They were then washed in the testing medium (Krebs or Modified Eagle's Medium (MEM), with 1% serum), and were rewrapped in foil and held for at least 39 minutes at room temperature.

FacScan

Using a Becton Dickenson FACSort cell sorter, the background tube mentioned above was used to set side scatter (SSC) and fluorescence intensity (FSC) parameters so that all unstained cells of the background control were visible in the SSC/FSC dot plot. The FL-1 parameters were set so that cells showed a fairly tight vertical distribution along the SSC axis. A first cell sample of approximately 10,000 labelled cells was stimulated in a 100 mg/dl glucose solution by adding an appropriate aliquot of glucose from a 15–30 mg/ml glucose solution. The tube was shaken lightly and the sample was immediately placed on the sample port to acquire flow cytometry data on the cells. The "Begin" switch was activated, and a scan was made of the cells, the dot plot of which is shown in FIG. 5A. The sample was similarly prepared at 300 mg/dl glucose and flow cytometry data similarly obtained for it. The dot plot is shown in FIG. 5B. It was noted that the greatest increase in cell number at the second concentration occurred at a fluorescent intensity just greater than about 20 on the X-axis, so the area labelled R1 was selected for sorting. While the cells could be scanned (or sorted) in the first 9 minutes or more after the glucose was added, it was preferred to scan them in the first 5, or more preferably the first 3 minutes. Cells sorted more than 10 minutes after labelling with glucose showed poorer insulin production and are labelled T6 on FIG. 6.

FACSort

Parameters were set so that all cells in R1 are selected. The above cells at about 300 mg/dl were then put into the sample port and a collection tube placed in the collection port, the "begin" switch activated, and the cells were sorted from the group. Sorting was accomplished in the time frames set forth above for the Sβ-1 cell line shown in FIG. 6; the T6 cell line was sorted after the cells remained in glucose more than 10 minutes.

Stability of Cell Line

The Sβ-1 cell line produced above was maintained in culture for 37–38 passages. At that time, it was tested for glucose responsiveness using the same assay mentioned above; it showed correct insulin regulation and a capacity to produce 4000–5000 μIU insulin/45 min/50,000 cells when stimulated by 16 mM glucose. A graph of these results is shown in FIG. 7.

Insulin Regulation in Sorted Cells

Sβ-1 cells at passage 37 were characterized in a stepped perifusion study after 24 hours in culture medium including IBMX. The results shown in FIG. 8 were normalized for DNA since the cells contain more DNA per cell than the islet cells used for comparison (see later discussion). The cells show almost 25 μIU insulin release per ml per μg DNA.

Adult mouse islet cells were similarly tested and also showed a peak at 16.7 mM glucose concentration. The results are shown in FIG. 9. Porcine islet cells were also tested over time but at a constant in glucose level as shown in FIG. 10. Porcine islet cells are of particular interest as a comparison because they are believed to closely mimic normal human cells and are therefore frequently used as a model for human islets. The porcine cells when exposed to insulin at high levels for about 2 hours show a brief peak at about 30 to 35 minutes and another peak at about 90 to 100 minutes. During the period from about 40 minutes to 90 minutes, they were shown to release a constant amount of insulin, specifically, about 60 μIU insulin/ml/mg of DNA.

Example 3: Selection of Slowly Dividing Cell Lines using Fluorescent-Activated Sorting and "Cell Link" Labeling Cells of the Sβ-1 subline produced by the fluorescence-activated sorting described above were trypsinized and washed with calcium- and magnesium-free Hanks' Balanced Salt Solution and centrifuged at 400× g for 5 minutes. Cells were then resuspended in 1 mil of (the same) diluent and mixed with 2× solution ($4 \times 10^{-6}$ mM) of the cell membrane market PKH26-GL and incubated for 2 to 5 minutes. Two mls of horse serum were added to quench the staining. After 1 minute in serum, 4 mls of complete Dulbecco's Modified Eagle's Medium (DMEM) were added and the solution centrifuged for 10 minutes at 400× g. The supernatant was aspirated and the wash procedure repeated a total of three times. The cells were returned to culture. The stained cultures were measured by flow cytometry on days 1, 5, 12 and 14 for remaining fluorescence (side scatter) and were then sorted. The data is presented in FIGS. 13A and 13B which illustrates side scatter on the vertical axis versus fluorescence intensity on the horizontal axis. A small population (about 1%) of highly fluorescent cells (gate=R4) were present after 14 (FIG. 13D) days in culture indicating the presence of very slowly dividing cell in the cultures.

To select for cells and produce a cell line showing high insulin production, a population of β cells, preferably an already sorted population such as the Sβ-1 line, is labeled as above, and the narrow band (gate=R4) of highly fluorescent cells is collected. These cells are returned to culture; after one week or more, the cells are harvested, the distribution of fluorescent intensity is determined and the most highly fluorescent (gate=R4) are sorted and placed in culture. This population is then assayed for insulin output and is expected to produce higher insulin levels while remaining correctly regulated.

Example 4: Method of Encapsulation of β-Cells

β-cell line cultures were prepared according to Example 1. After 10–30 passages in culture, the cells are harvested using a sterile pipet. Cells are washed in CMRL 1066™ (Gibco) and resuspended in CMRL 1066 (Gibco) to a concentration of 25 million/ml. A 2% solution of sodium alginate is prepared under sterile conditions. The cells are diluted 1:1 with the alginate solution, for a final concentration of 1% alginate in the islet suspension. The cells are hand-loaded into a PAN/PVC permselective hollow fiber membrane according to the method of Dionne in U.S. patent application Ser. No. PCT/US92/03327, filed on Apr. 2, 1992, which is incorporated herein as though fully set forth. The fiber devices are sealed and placed in a 1% calcium chloride solution to cross link the alginate. The fibers are placed in CMRL 1066 overnight. The fibers are tested for glucose responsivity by static and perifusion challenge with 0.1, 3.3, 8.3, 16.7 mM glucose.

The encapsulation procedure was also performed for parent β-TC-6 cells at about passages 15 to 17 (during which they are known to be correctly regulated). Correct regulation and a standard sigmoidal curve for glucose responsiveness was found in two of the three batches tested. Also, maximum insulin release at high glucose levels was found.

Example 5: Implantation of Encapsulated Cells into the Mouse

Based on the information obtained above relating to insulin secretion, and the insulin requirements of the mouse, it was determined that approximately 7 million cells need to be implanted in a mouse to maintain the mouse normoglycemic. The volume of this number of cells is about 10 μl. At a final cell density (after proliferation) of about 7–10% by volume, it was determined that approximately seven hollow fibers of 1000 μm i.d. and about 2.5 cm long are required to be implanted.

A correctly glucose responsive β-cell line was prepared according to Example 1 or 2. Cells are encapsulated according to Example 3. Devices are implanted intraperitoneally into streptozotocin-induced diabetic mice. Plasma glucose levels are monitored daily. After 60 days, the devices are removed and the mice are checked for a return to hyperglycemia. The recovered devices are assessed for the ability to release insulin in response to glucose perifusion.

Example 6: Implantation of Encapsulated β-cells in Human Subject

Based on insulation rates of the cells used and the amount of insulin needed to maintain normoglycemia over a 24 hour period in a human patient, it was determined that about 600–700 million cells need to be implanted to maintain a human normoglycemic. To produce this number of cells once proliferation has occurred, approximately 17 million cells of the above need to be implanted. Thus, 10 6 cm diameter flat sheets are required, containing, after proliferation, 65 million cells each, to release 40–60 IU insulin/day. 70 µl of an alginate cell slurry containing 25 million cells/ml is to be evenly spread throughout each device.

A β-cell suspension in alginate is prepared according to Example 3, at a density of 25 million cells/ml. Seventy microliters are loaded into each of 10 flat sheet devices, each having a surface area of 70 cm² (including both sides) and are sealed according to the method disclosed in U.S. patent application Ser. No. 08/082,407, filed Jun. 23, 1993, incorporated herein as though fully set forth.

The devices are implanted in peritoneal cavity, preferably in and around lobes of the liver. After implantation, intensive insulin treatment (2–4 shots of insulin and 10–15 glucose checks per day) is maintained for 2 weeks. Exogenous insulin is slowly tapered off as cell number increases and more insulin is released from the devices. Patients are removed from insulin and returned to normal glucose monitoring 1–2 months post implantation.

Example 7: Effect of Other Agents on Insulin Secretion

All insulin assays performed on the cells reported herein were done in the presence of 0.5 mM IBMX. IBMX is a potent enhancer of insulin secretion, which does not change the regulatory characteristics of β TC cells. Efrat et al, 1993 has shown that IBMX potentiates insulin release up to approximately 3-fold. However, if cells are to be used in vivo where they will not be exposed to IBMX, there are a number of other secretagogues and secretion enhancers which circulate systemically. These include glucagon, gastric inhibitory peptide, and the amino acids leucine and arginine. Therefore, it was also of interest to see if a cocktail of these natural agents when presented to the β cells of the present invention at physiologically relevant concentrations would enhance insulin secretion in vitro.

F7-1 cells were plated at a concentration of 50,000 cells/ml according to standard insulin assay conditions and were assayed as described in Example 1 except that in some cases the preincubation buffer contained either 0.5 mM IBMX or a secretagogue cocktail which consisted of:

0.013 mg/ml leucine
0.014 mg/ml arginine
0.016 mg/ml phenylalanine
0.001 µg/ml growth hormone
0.3 µg/ml glucagon
2 ng/ml gastric inhibitory peptide At 16 mM glucose, the secretagogue cocktail was approximately half as potent as IBMX alone, indicating that these cells are likely to have enhanced insulin secretion in vivo as compared to in vitro Additionally, the enhancement of insulin secretion by IBMX at 16 mM glucose was less than two-fold.

It will be understood that the above discussion is intended by way of description and not by way of limitation and that many other embodiments will be apparent to those of skill in the art and will fall within the scope of the invention as defined by the appended claims.

What is claimed is:

1. A cell culture comprising selected β-cells produced] having enhanced secretion of insulin, said β-cells selected by the following steps:

(a) providing a population of cells comprising β-cells in which increased intracellular concentrations of calcium ions is correlated with the extracellular presence glucose;

(b) exposing said population of cells to a vital calcium-activated labelling agent;

(c) exposing said population of cells to glucose in concentration sufficient to result in secretion of insulin;

(d) selecting from the population, cells that exhibit increased amounts of intracellular free calcium when exposed to said glucose in step (e); and (f) culturing said selected cells.

2. A cell culture according to claim 1 wherein immediately prior to step (c) said population of cells is exposed to glucose at levels in the range of about 3 mM to 9 mM and wherein the population of cells of step (c) are exposed to glucose at a concentration greater than about 10 mM; and step (d) includes the steps of (i) providing a fluorescence-activated cell sorter; (ii) using the sorter, identifying a small group of cells of fluorescing at an intensity above a pre-selected amount; (iii) using the sorter, selecting the group of cells from the population of step (c) having a fluorescent intensity above the pre-selected amount, said pre-selected fluorescent intensity being selected so that about 50% as many cells are selected in step d (iii) as are shown to have more than the pre-selected intensity in step d (ii).

3. A β-cell line having enhanced secretion of insulin, wherein said β-cells have been selected by the following steps:

(a) providing a population of cells including cells in which increased intracellular concentrations of calcium ions is correlated with the extracellular presence of glucose;

(b) exposing the population of cells to a vital calcium-activated labelling agent;

(c) exposing the population to glucose in concentration sufficient to result in secretion of the insulin;

(d) selecting from the population, those cells which exhibit increased amounts of intracellular free calcium when exposed to said glucose in step (c);

(e) culturing the selected cells;

(f) exposing the cultured, selected cells to a cell membrane;

(h) proliferating the selected cells; and (i) selecting cells proliferated in step (h) that show a half-life for the decay of fluorescence intensity of about 30% or more than the mean doubling time of said cultured, selected cells of step (e).

4. A population of correctly regulated β-cells produced by the following steps:

(a) providing a population of β cells; and
(b) selecting from said population, the cells which secrete approximately twice as much insulin when stimulated by glucose at a first concentration at a point above about 10 mM as they do when stimulated by glucose at a second concentration at a point in the range of about 3 mM to about 9 mM, wherein said selection is performed by the following steps:
  i. exposing said cells to a dye which labels intracellular calcium;
  ii. exposing said cells to glucose at the second concentration;
  iii. exposing the cells to glucose at the first concentration;
  iv. defining a group of cells showing more labelling at said first concentration than at said second concentration; and
  v. selecting the group of cells from step (d) which show more labelling.

5. A line of correctly regulated β-cells produced by the following steps:

(a) providing a population of β cells; and
(b) selecting from said population, the cells which secrete approximately twice as much insulin when stimulated by glucose at a first concentration at a point above about 10 mM as they do when stimulated by glucose at a second concentration at a point in the range of about 3 mM to about 9 mM, wherein said selection is performed according to the following steps:
  i. dissociating the cells in the population;
  ii. proliferating the dissociated cells;
  iii. culturing the proliferated dissociated cells to produce clones;
  iv. determining the insulin production of said clones at said first concentration and said second concentration; and
  v. selecting those clones secreting at the first concentration, about twice the insulin secreted at the second concentration.

* * * * *

UNITED STATES PATENT AND TRADEMARK OFFICE
CERTIFICATE OF CORRECTION

PATENT NO. : 5,712,159
DATED : Jan. 27, 1998
INVENTOR(S) : Laurence et al.

It is certified that error appears in the above-identified patent and that said Letters Patent is hereby corrected as shown below:

In the first line of Claim 1, at col. 18, line 11, the term "produced]" should be deleted.

Signed and Sealed this

Twenty-ninth Day of September, 1998

Attest:

BRUCE LEHMAN

Attesting Officer      Commissioner of Patents and Trademarks